United States Patent
Johnson et al.

(10) Patent No.: US 7,637,922 B2
(45) Date of Patent: Dec. 29, 2009

(54) CALF COMPRESSION DEVICES

(75) Inventors: Richard Johnson, Cardiff (GB); Nile Allaf, Cardiff (GB)

(73) Assignee: Novamedix Distribution Limited (GB)

( * ) Notice: Subject to any disclaimer, the term of this patent is extended or adjusted under 35 U.S.C. 154(b) by 813 days.

(21) Appl. No.: 10/498,595

(22) PCT Filed: Dec. 10, 2002

(86) PCT No.: PCT/GB02/05585

§ 371 (c)(1), (2), (4) Date: Nov. 24, 2004

(87) PCT Pub. No.: WO03/053323

PCT Pub. Date: Jul. 3, 2003

(65) Prior Publication Data

US 2005/0070954 A1    Mar. 31, 2005

(30) Foreign Application Priority Data

Dec. 11, 2001  (GB) ................. 0129554.2
Sep. 10, 2002  (GB) ................. 0220923.7

(51) Int. Cl.
*A61B 17/00* (2006.01)
*A61H 19/00* (2006.01)

(52) U.S. Cl. .................. 606/201; 601/152; 606/202

(58) Field of Classification Search ......... 606/201, 606/202, 203; 601/152; 604/66, 540
See application file for complete search history.

(56) References Cited

U.S. PATENT DOCUMENTS

| 4,715,849 A | * | 12/1987 | Gion et al. ............. 604/540 |
| 4,841,956 A | * | 6/1989 | Gardner et al. .......... 601/152 |
| 4,865,020 A | * | 9/1989 | Bullard ................. 601/152 |
| 5,309,908 A | * | 5/1994 | Friedman et al. ........ 600/322 |
| 5,352,195 A | * | 10/1994 | McEwen ................. 604/66 |

(Continued)

FOREIGN PATENT DOCUMENTS

EP    0 861 651 A1    9/1998

(Continued)

OTHER PUBLICATIONS

Pekanmaki et al., "Sequential and Graded Intermittent Pneumatic Compression Device for Treatment of Swollen Limbs", Biomedizinische Technik, vol. 32, No. 3, Mar. 1987, p. 50-54, Fachverlag Schiele Und Schoen Gmbh, Berlin, Germany.

*Primary Examiner*—Long V Le
*Assistant Examiner*—Angela M Hoffa
(74) *Attorney, Agent, or Firm*—Baker & McKenzie LLP

(57) ABSTRACT

There is provided a calf compression device for reducing the risk of deep vein thrombosis which comprises an inflatable cuff (100, 200) adapted to be wrapped around the whole or part of a calf of a human person and a pump (104, 204) capable of first inflating the cuff (2) and then deflating the cuff over a regular repeating cycle, said repeating cycle comprising rapidly inflating the cuff (100, 200) to a pressure of between 40 and 70 mm mercury above ambient, maintaining the pressure for 10 to 15 seconds, deflating the cuff (100, 200) over a period of 40 to 50 seconds and then repeating the cycle by rapidly inflating the cuff (100, 200) within 10 seconds of commencement of the cycle.

6 Claims, 3 Drawing Sheets

U.S. PATENT DOCUMENTS 5,891,065 A      4/1999   Cariapa et al.
6,475,228 B1 *  11/2002  Mesaros et al. ............. 606/202
6,494,852 B1 * 12/2002  Barak et al. ................. 601/151

FOREIGN PATENT DOCUMENTS

WO      WO 94/12141          6/1994
WO      WO 00/72797 A1     12/2000

* cited by examiner

CALF COMPRESSION DEVICES

This is a national phase application of International Application PCT/GB02/05585, filed Dec. 10, 2002, and claims priority to United Kingdom Patent Application No. 0129554.2, filed Dec. 11, 2001 and United Kingdom Patent Application No. 0220923.7, filed Sep. 10, 2002. This invention relates to calf compression devices, methods of reducing the risk of deep vein thrombosis, portable devices for reducing the risk of deep vein thrombosis, articles for accommodating persons wishing to use such devices, kits and relating thereto and to electric pumps. This invention is particularly, though not exclusively, concerned with, devices for alleviating deep vein thrombosis.

A significant cause of death is thrombosis, that is the formation of a blood clot or thrombus in a normal blood vessel. The blood clot is probably caused by platelets aggregating at and adhering to the site of an injury in the blood vessel. The aggregation may be reinforced by fibrin and such a thrombus can severely restrict or block the flow of blood in the blood vessel. Whilst such a thrombus may not even be detected in small veins, the blood may entirely clot to form a larger mass. The danger from such a thrombus is that it may become detached and be swept into a vital organ, in particular, the lung where it may cause a disastrous circulatory obstruction. The most commonly occurring thrombotic indications are clots in the leg veins (deep vein thrombosis, sometimes referred to as DVT) and in the lung (pulmonary embolism).

A principal cause of thrombosis is a slowing of blood flow in a number of circumstances. These include confinement to bed or lack of exercise. The problem is exacerbated by other factors such as for example, obesity, malignant disease and blood dyscrasias. DVT may also affect persons of any age, but, in particular, those in older age groups. It may also present a problem in post-operative recovery stages. Of major concern is a period of prolonged inactivity such as during long confinement in an aeroplane, where there is a tendency to sit in cramped conditions relatively inert in an immobile position often for many hours. Furthermore the atmosphere in an aeroplane is often conducive to such inactivity—low cabin pressure, reduced oxygen content and availability of alcohol. This leads to blood pooling in the lower extremities, i.e. in the stem veins of the lower limb. The apparent increase in instances of DVT as a result of air travel (sometimes referred to as "Economy class syndrome") is a major cause of concern, in particular amongst frequent flyers. This has resulted in airlines issuing charts giving details of in flight exercises. However such exercises are often inconvenient because of for instance, interference with cabin staff scheduling, neighbour disturbance.

Whilst DVT may be of most topical concern in relation to air travel, it may also a problem in any situation where there is prolonged restriction of movement. These situations include long journeys by train and car, persons who have restricted movement due to age and/or ill health, for example, the wheel chair bound.

Thrombosis can be alleviated by medication. Many medicines are available for prescription or hospital use such as for example, warfarin which inhibits clot formation; streptokinase, urokinase, tissue plasminogen activators which dissolve clots; fibrinolytic agents. A commonly used agent is aspirin in low doses. However the use of any of the above medications can be associated with side effects such as bleeding in the digestive tract.

There is therefore a need for a device that can assist in the avoidance of DVT.

Blood pressure is most often measured using a sphygmomanometer. The pressure of blood within an artery is balanced against an external pressure applied to a cuff which is wrapped around an arm. Thus the cuff is wrapped around an arm, the cuff inflated with air from a squeezable bulb and the pressure of air in the cuff is increased sufficient to stop the flow of blood in the artery as heard in an stethoscope placed on the arm below is the cuff. Air is gradually released from the cuff through a manually operated valve and the air pressure noted at which blood starts to flow as judged by a soft heart beat (systolic blood pressure); on further releasing the air pressure, that at which the heartbeat disappears is also noted (diastolic blood pressure).

According to the present invention a calf compression device for reducing the risk of deep vein thrombosis is provided which comprises an inflatable cuff adapted to be wrapped around the whole or part of a calf of a human person and a pump capable of first inflating the cuff and then deflating the cuff over a regular repeating cycle, said repeating cycle comprising rapidly inflating the cuff to a pressure of between 40 and 70mm mercury, maintaining the pressure for 10 to 15 seconds, deflating the cuff over a period of 40 to 50 seconds and then repeating the cycle by rapidly inflating the cuff within 10 seconds of commencement of the cycle.

The cuff can be fabricated from any material known in the sphygmomanometer. Generally it will be fabricated from for example from flexible synthetic or natural rubber, or fabric impregnated with a polymeric material to render the material essentially impervious to air. The cuff may be, for example, a gas impermeable balloon or tube, for example, located within a sock or tubular sleeve. The cuff preferably comprises a single chamber, but may comprise a plurality of chambers; however in accordance with the present invention the plurality of chambers are joined internally or externally and preferably all, but at least some or most, are filled at the same time and not sequentially. The cuff is provided with a connector or flexible pipe so that it may be inflated or deflated.

The cuff is preferably shaped to fit the calf. The cuff will be provided with means to retain the cuff in position on the calf. Such means may be for example lacing ties, buckle and strap but are preferably fastening straps made from self fastening material, for example, Velcro™ and similar materials, or if the cuff is in the form of a sock or sleeve, the fabric may be elasticated so that the cuff is retained in position on the calf. However the cuff is essentially inextensible so that inflation causes the cuff to press on the calf rather than merely expand only at the surface distal from the calf. Preferably the cuff is reusable, and washable. It will be understood that the cuff will be provided with at least one tube to allow ingress and egress of air. The cuff may be provided in different sizes so as to accommodate calves of different length and thickness.

In accordance with the present invention the cuff is to be inflated and deflated over a regular repeating cycle. The cycle comprises inflation of the cuff over a period of 1 to 12 seconds to a pressure of between 40 and 70 mm mercury, preferably 50 to 60 mm mercury, maintaining the pressure for 10 to 15 seconds, preferably 11 to 14 seconds, and deflating to ambient pressure, but preferably to a pressure of between 5 and 15mm mercury above ambient, over a period of 40 to 50 seconds. Deflation enables complete refilling of the veins, but deflation to a pressure above ambient reduces the amount of venous filling and reduces power supply drain. It is important that the inflation step is effected rapidly, that is within 10 seconds of commencement of the cycle, preferably within 5 seconds. Such a complete cycle will generally last for 40 to 90 seconds, preferably 50 to 70 seconds, and is repeated for as long as the pump is activated. By the term "ambient pressure"

is generally meant atmospheric pressure, but in some situations, such as in an aeroplane, cabin pressure may be different and hence the term means the local pressure. In this cyclical process, local venous blood flow is improved and normal physiological venous return from the leg or legs is augmented. The risk of developing DVT is thereby reduced.

The cyclical process is facilitated by a pump. The pump supplies gas, generally air from the local environment, to inflate the cuff, and is preferably battery driven and should be small. The pump can be located, as can its power supply, in the clothing of the person; it may be located on the cuff itself but this likely to be less convenient because of physical interference with movement of the person. If the present devices become generally available, it is envisaged that aircraft seats may provide a plug-in power supply. The pump is conveniently connected to the cuff by flexible tubing fitted with coupling connectors to facilitate connection for use and disconnection when not in use. The pump provides pressurisation of the cuff, and may be provided with a release valve to allow slow release of air during deflation. The pump may be provided with a pressurisation valve which controls pressurisation of the cuff. In another embodiment of the present invention, the cuff may be provided with an internal or externally connected valve to release air during the deflation phase, but operation of such a valve should act in phase with the inflation pump so as to provide a cycle hereinbefore described. Preferably the pump includes the release valve and any pressurisation valve. The pump may also include controls for varying the length of the cycle and any phase within that cycle, but preferably such variables are preset. The cyclical process continues until the power source is turned off, and starts up when the power source is turned on.

The power supply for the pump, and any electrically operated ancillary equipment such as, for example, valves, is conveniently a battery attached to or adjacent the pump. By the term "adjacent" is meant located closeby the pump so that a cable connection can be made to the battery or battery outlet. The battery, preferably rechargeable, can be any type which can supply electrical power to the pump over a prolonged period, for example 1 to 6 hours, and is preferably based on metal hydride technology. When the power supply is located attached or even adjacent to the pump (for example, in a pocket in clothing worn by the user), the device of the invention is totally portable. Convenient voltages for the power supply are those commonly used in cars, lorries and aeroplanes, for example 12 volts and 24 volts direct current or 28 volts, 115volts or 230 volts alternating current, and these power supplies may be used to recharge or augment the battery (with rectification and voltage reduction as appropriate). The power supply may also be a mains source which is adapted to power the pump and recharge the battery; this is particularly convenient of the patient requires prolonged treatment by the device and hence is located at a single place for a period between the requirement for portability, for example a wheel chair patient. Most conveniently the battery, pump and valves are housed in a single housing which may be, for example, designed to be accommodated in clothing.

Accordingly, the combination of cuff, pump, release valve and power supply is provided with a pressure sensor device and a timer which (i) at the start of the cycle initiates the pump which continues to pressurise the cuff until the required pressure is attained as determined by the pressure sensor device over a predetermined period, (ii) switches off the pump, (iii) holds closed the release valve for a required period, and then (iv) opens the release valve so as to release air from the cuff to deflate the cuff at a required rate to a pressure determined by the pressure sensor device.

According to a further aspect of the present invention, a portable device is provided for reducing the risk of deep vein thrombosis which comprises an inflatable cuff adapted to be wrapped around the whole or part of a calf of a human person, a pump and a battery for the pump, said pump capable of first inflating the cuff and then deflating the cuff over a regular repeating cycle, said repeating cycle comprising rapidly inflating the cuff to a pressure of between 40 and 70mm mercury, maintaining the pressure for 10 to 15 seconds, deflating the cuff over a period of 40 to 50 seconds and then repeating the cycle by rapidly inflating the cuff within 10 seconds of commencement of the cycle.

In a further embodiment of the present invention, there is provided an electric, preferably battery-driven, pump and associated timing device adapted to deliver air rapidly to an external closed system to a pressure of between 40 and 70 mm mercury, preferably 50 to 60 mm mercury, to maintain that pressure for 10 to 15 seconds, and then to deflate the external closed system over a period of 40 to 50 seconds and then repeating the cycle by rapidly inflating the cuff within 10 seconds of commencement of the cycle.

In a further embodiment of the present invention, a method of reducing the risk of DVT is provided which comprises positioning and securing an inflatable cuff around a calf, rapidly inflating the cuff to a pressure of between 40 and 70 mm mercury, maintaining the pressure for 10 to 15 seconds, and deflating over a period of 40 to 50 seconds, and then repeating the cycle by rapidly inflating the cuff within 10 seconds of commencement of the cycle.

In a further embodiment of the present invention, a kit or pack of two such devices is provided. In an alternative embodiment, a kit is provided comprising two cuffs and a single pump, so that the pump can pump each cuff in out of phase cycles. Such an embodiment leads to a more efficient use of the power supply which is particularly important where the power supply is battery based.

It will be understood that the pump and/or its power supply might be a fixed facility in an article which accommodates the person wishing to use the device of the invention. Such an article includes for example a wheel chair, a bed, a car, a car seat, an aeroplane seat, and further embodiments of this invention include such articles. In accordance therefore with a further aspect of the present invention an article for accommodating a person wishing to use the device is provided which includes at least one component selected from a dedicated power supply, power supply, pump and timer.

The present invention will now be described, by way of example only, with reference to the drawings that follow; in which.

Figure 1:
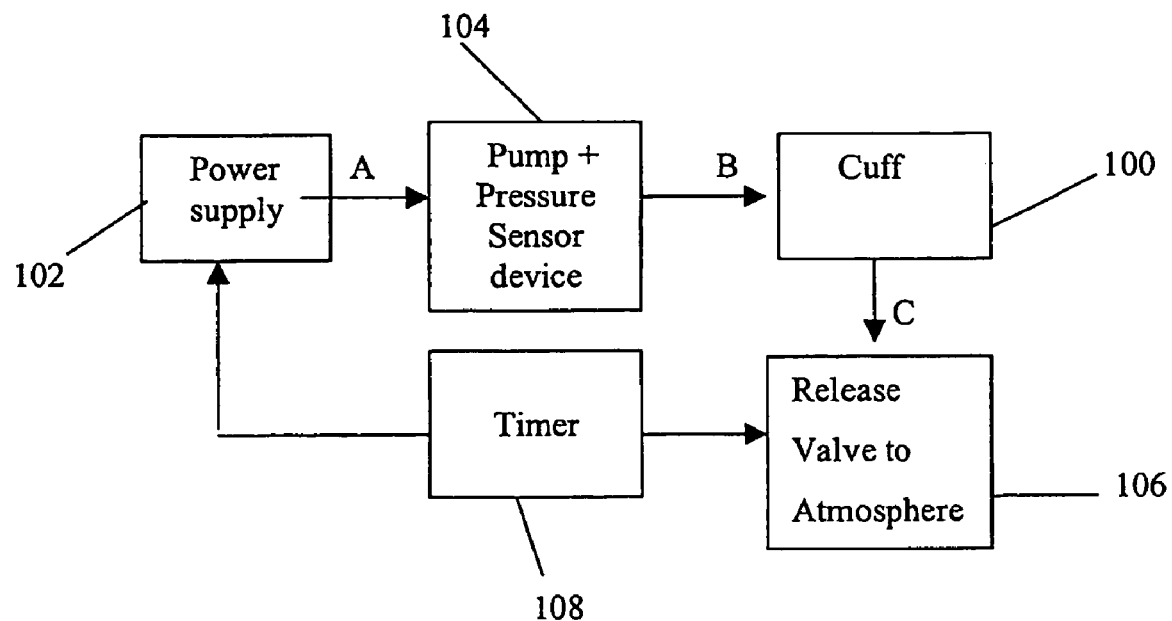
FIG. 1 is a diagrammatic illustration of a method and apparatus according to an embodiment of the present invention.

In FIG. 1, a cuff 100 is inflated by air pumped through flexible tubing B when power is supplied from a power supply 102 through cabling A. A pump 104 cuts out when the pressure in the cuff 100 as has reached the required pressure. A pressure sensor device is preferably provided in the cuff 100 or pump 104 to shut off the flow of air from the pump 104. A Release Valve 106 is provided with a timer 108 so that after a required period the cuff 100 is deflated through the Release Valve 106 via flexible tubing C. The timer 108 also repeats the cycle after deflation provided that the power supply 102 is still switched on.

Figure 2:
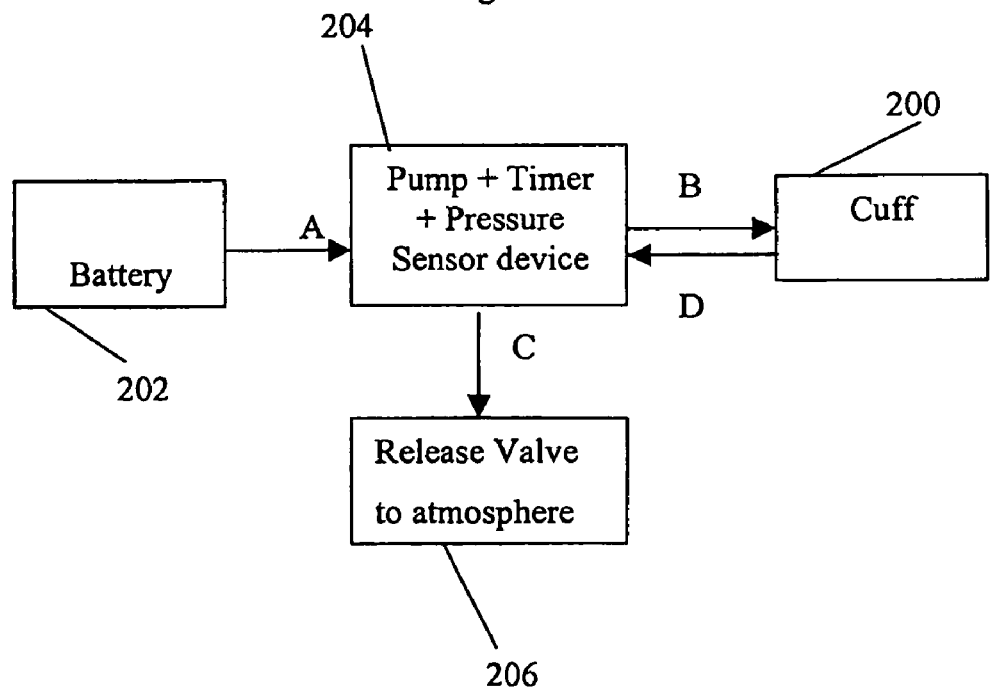
FIG. 2 is a diagrammatic illustration of a method and apparatus according to another embodiment of the present invention.

In FIG. 2, a Pump 204 and Timer 204 are interconnected in the same unit and provided with an outlet to inflate a cuff 200 through flexible tubing B and inlet for deflating the cuff 200 though flexible tubing D. A pressure sensor device 204 is preferably provided in the pump 204 to shut off the flow of air from the pump 204. The Pump 204 and Timer unit 204 is provided with a further outlet for controlling a Release Valve 206. In a preferred embodiment, a Battery 202, Pump 204, Timer 204 and Release Valve 206 are provided in the same unit, thereby minimising physical size of the device of the invention and providing optimum control of the cycle. Flexible tubing B and D may be co-axial or laterally joined so as to provide single connecting tubing.

In both the embodiments of FIGS. 1 and 2, one or more of the components as appropriate other than the cuff 100, 200 can be provided on the article in or on which the person is accommodated. Hence the Power Supply, Power Supply and Pump, or Power Supply and Pump and Timer may be on or in a bed, car seat, car dashboard or aeroplane seat.

Figure 3:
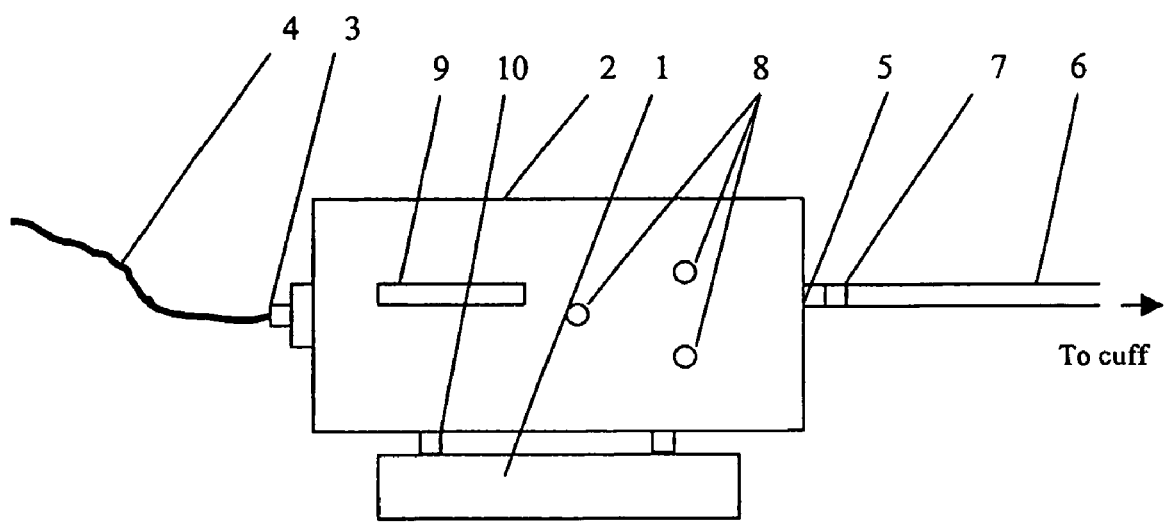
FIG. 3 is a schematic illustration of an apparatus according to an embodiment of the present invention.

FIG. 3 shows an arrangement of power supply and a pump. A battery 1 is physically attached a pump 2 through attachments 10, either or both of which may include electrical connectors. The pump 2 has an inlet electrical socket 3 for connection through cable 4 to an external mains supply, typically 230 volts or 110 volts. The pump and battery unit is provided with electrical circuitry which enables the mains supply voltage to be reduced and rectified (if alternating current) so as to power the pump and recharge the battery. The pump is provided with an outlet 5 for connection to a cuff (not shown) via a flexible conduit 6 which it itself fitted with a co-operating connector 7. The pump unit is also fitted with an air inlet, pressurisation valve, a release valve, a pressure sensor for determining when air should be fed to and released from the cuff, and a timer. Controls 8 allow for variation in pressurisation and release pressures and cycle timings; panel 9 is a battery charge state indicator.

Alternatively the battery may be located within the pump housing. Alternatively, the external power supply may be a direct current source which can power the pump and recharge the battery. Alternatively, the pressurisation and release pressures and cycle timings can be preset.

In operating the device, an inflatable cuff is located and secured to the calf of a patient, and connected to the device through conduit 6 by connectors 6 and 7. The battery 1 having been precharged, the pump 2 switched on to start the cycle and the cuff is inflated over a predetermined period controlled by the timer to a pressure determined by the pressure sensor. On attaining that pressure the pump is switched off by the timer, pressure maintained in the cuff for a predetermined period. The pressure is then released over a given period through the release valve until a predetermined pressure has been reached. The cycle is then repeated for so long as the power supply is maintained.

Figure 4:
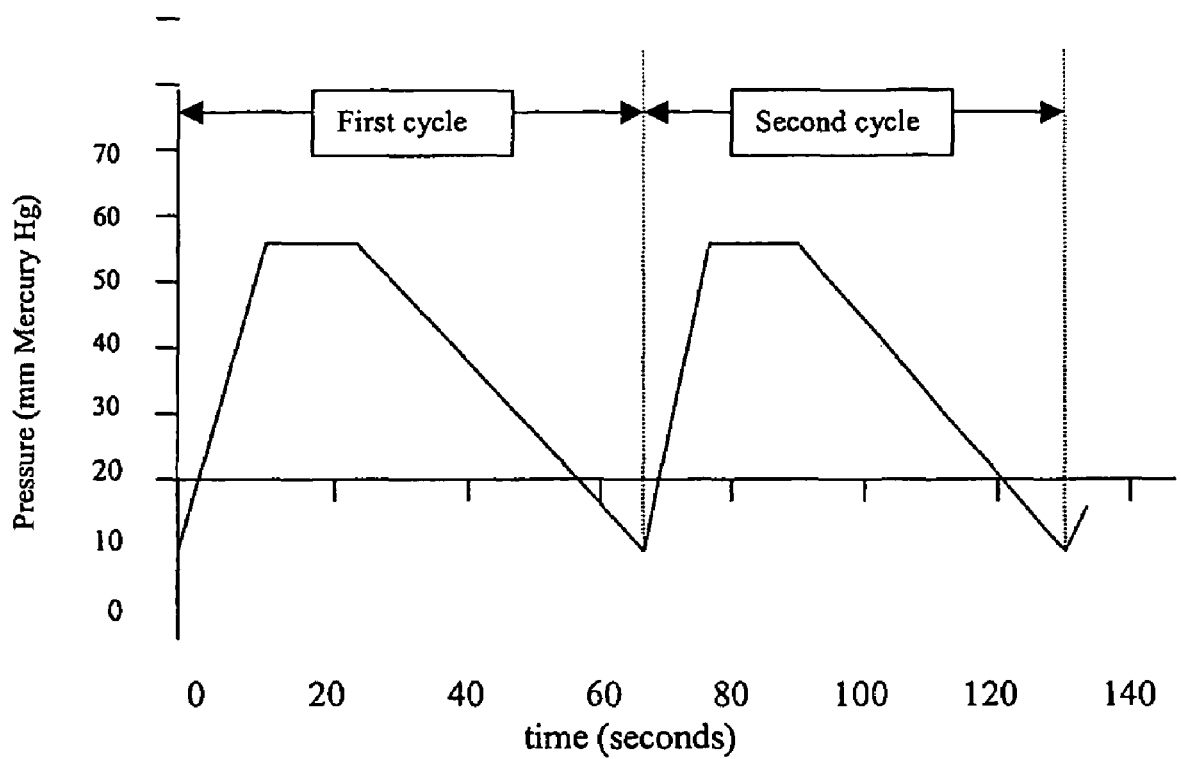
FIG. 4 is a graph illustrating two successive cycles of an apparatus according to an embodiment of the present invention.

FIG. 4 shows an example of two typical successive cycles of the device of the invention from the data in Table 1.

TABLE 1

| | Time (seconds) | | | | | | |
|---|---|---|---|---|---|---|---|
| | 0 | 10 | 22 | 65 | 75 | 87 | 130 |
| Cuff pressure (mm Hg) | 10 | 55 | 55 | 10 | 55 | 55 | 10 |

Table 1 gives the pressure above ambient in the cuff at given times in the cycles. In this example, the cycle time is 65 seconds, and the pressure of 55 mm Hg is rapidly reached from 10mm Hg in 10 seconds and held at that pressure for 12 seconds before slowly decreasing to 10 mm Hg over 43 seconds. FIG. 1 is a plot of the data in Table 1.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A calf compression device for reducing the risk of deep vein thrombosis, the device comprising:
   a first inflatable cuff adapted to be wrapped around the whole or part of a first calf of a human person;
   a second inflatable cuff adapted to be wrapped around the whole or part of a second calf of a human person; and
   a pump configured to inflate and deflate the first cuff and the second cuff over a regular repeating cycle, said repeating cycle comprising:
      a first inflation period of no more than 10 seconds wherein the first cuff is inflated to a pressure of between 40 and 70 mm mercury above ambient;
      a first pressure maintenance period of between 10 and 15 seconds wherein the pressure in the first cuff is maintained, the first pressure maintenance period immediately succeeding the first inflation period;
      a first deflation period of between 40 and 50 seconds wherein the first cuff is deflated, the first deflation period immediately succeeding the first pressure maintenance period;
      a second inflation period of no more than 10 seconds wherein the second cuff is inflated to a pressure of between 40 and 70 mm mercury above ambient, the second inflation period occurring within the combined first pressure maintenance period and first deflation period;
      a second pressure maintenance period of between 10 and 15 seconds wherein the pressure in the second cuff is maintained, the second pressure maintenance period immediately succeeding the second inflation period;
      a second deflation period of between 40 and 50 seconds wherein the second cuff is deflated, the second deflation period immediately succeeding the second pressure maintenance period; and a repeated first inflation period immediately succeeding the first deflation period, the repeated first inflation period occurring within the combined second pressure maintenance period and second deflation period.

2. A device according to claim 1, wherein the device is configured such that the first inflation period is no more than 5 seconds, and the second inflation period is no more than 5 seconds.

3. A device according to claim 1, wherein the device is configured such that the first cuff is deflated to a pressure of 10 mm mercury above ambient during the first deflation period, and the second cuff is deflated to a pressure of 10 mm mercury above ambient during the second deflation period.

4. A device according to claim 1, wherein the device is configured such that the first cuff is inflated to a pressure of between 50 and 60 mm mercury above ambient during the first inflation period, and the second cuff is inflated to a pressure of between 50 and 60 mm mercury above ambient during the second inflation period.

5. A device according to claim 1, wherein the device is configured such that the first pressure maintenance period is between 11 and 14 seconds, and the second pressure maintenance period is between 11 and 14 seconds.

6. A device according to claim 1, wherein the device is configured such that a first cycle period comprising the first inflation period, the first pressure maintenance period, and the first deflation period is between 50 and 70 seconds, and a second cycle period comprising the second inflation period, the second pressure maintenance period, and the second deflation period is between 50 and 70 seconds.

* * * * *